(12) United States Patent
Xue et al.

(10) Patent No.: US 12,303,545 B2
(45) Date of Patent: May 20, 2025

(54) **POLYPEPTIDE WITH ANTI-*MYCOBACTERIUM TUBERCULOSIS* ACTIVITY, AND PREPARATION METHOD AND USE THEREOF**

(71) Applicant: AGRICULTURAL UNIVERSITY OF NANJING, Nanjing (CN)

(72) Inventors: Feng Xue, Nanjing (CN); Hao Sun, Nanjing (CN); Quntao Huang, Nanjing (CN); Jinglin Song, Nanjing (CN)

(73) Assignee: AGRICULTURAL UNIVERSITY OF NANJING, Nanjing (CN)

( * ) Notice: Subject to any disclaimer, the term of this patent is extended or adjusted under 35 U.S.C. 154(b) by 0 days.

(21) Appl. No.: 18/824,970

(22) Filed: Sep. 5, 2024

(65) Prior Publication Data

US 2024/0415925 A1 Dec. 19, 2024

Related U.S. Application Data

(63) Continuation of application No. PCT/CN2023/140163, filed on Dec. 20, 2023.

(30) Foreign Application Priority Data

Jun. 15, 2023 (CN) .......................... 202310710031.5

(51) Int. Cl.
| | | |
|---|---|---|
| *A61K 38/16* | (2006.01) | |
| *A61K 38/00* | (2006.01) | |
| *A61K 45/06* | (2006.01) | |
| *C07K 7/08* | (2006.01) | |
| *C07K 14/00* | (2006.01) | |

(52) U.S. Cl.
CPC ............ *A61K 38/16* (2013.01); *C07K 14/001* (2013.01)

(58) Field of Classification Search
CPC ........ A61K 38/00; A61K 38/16; A61K 45/06; C07K 7/08; C07K 14/00; C07K 14/001
See application file for complete search history.

(56) References Cited

U.S. PATENT DOCUMENTS

| | | | | |
|---|---|---|---|---|
| 2014/0296137 A1* | 10/2014 | Rajamani | ............... | A01N 63/50 514/4.5 |
| 2015/0259382 A1 | 9/2015 | Wang | | |
| 2018/0355005 A1 | 12/2018 | Kao et al. | | |

FOREIGN PATENT DOCUMENTS

| | | |
|---|---|---|
| CN | 109762051 A | 5/2019 |
| CN | 109897091 A | 6/2019 |
| CN | 116987149 A | 11/2023 |
| WO | 2023049162 A1 | 3/2023 |

OTHER PUBLICATIONS

Kanjana Madhingsa, et al., Antimicrobial Action of the Cyclic Peptide Bactenecin on Burkholderia pseudomallei Correlates with Efficient Membrane Permeabilization, PLOS Neglected Tropical Diseases, 2013, pp. 1-13, vol. 7 No. 6.

* cited by examiner

*Primary Examiner* — Julie Ha
(74) *Attorney, Agent, or Firm* — Bayramoglu Law Offices LLC

(57) ABSTRACT

A polypeptide with an anti-*Mycobacterium tuberculosis* activity, and a preparation method and use thereof are provided. The preparation method of the polypeptide includes the following steps: (1) preparing a straight-chain polypeptide with a sequence shown in SEQ ID NO: 1; and (2) allowing sulfhydryl groups of two cysteine residues in the straight-chain polypeptide to undergo a dehydration-condensation reaction with dimethylourea to obtain the polypeptide. The polypeptide has little cytotoxicity and a prominent anti-*Mycobacterium tuberculosis* effect.

9 Claims, 14 Drawing Sheets

Specification includes a Sequence Listing.

SEQUENCE LISTING

```
Sequence total quantity: 3
SEQ ID NO: 1            moltype = AA   length = 18
FEATURE                 Location/Qualifiers
source                  1..18
                        mol_type = protein
                        organism = synthetic construct
SEQUENCE: 1
GRFCRFRCKF KKLFKKLS                                                  18

SEQ ID NO: 2            moltype = AA   length = 18
FEATURE                 Location/Qualifiers
source                  1..18
                        mol_type = protein
                        organism = synthetic construct
SEQUENCE: 2
GRFKRFRKKF KKLFKKLS                                                  18

SEQ ID NO: 3            moltype = AA   length = 18
FEATURE                 Location/Qualifiers
source                  1..18
                        mol_type = protein
                        organism = synthetic construct
CROSSLNK                4..8
                        note = the two cysteines are linked by dimethylolurea
SEQUENCE: 3
GRFCRFRCKF KKLFKKLS                                                  18
```

POLYPEPTIDE WITH ANTI-*MYCOBACTERIUM TUBERCULOSIS* ACTIVITY, AND PREPARATION METHOD AND USE THEREOF

CROSS REFERENCE TO THE RELATED APPLICATIONS

This application is a continuation application of International Application No. PCT/CN2023/140163, filed on Dec. 20, 2023, which is based upon and claims priority to Chinese Patent Application No. 202310710031.5, filed on Jun. 15, 2023, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBHS013-PKG_Sequence_Listing_20250206.xml, created on Feb. 6, 2025, and is 4,151 bytes in size.

TECHNICAL FIELD

The present disclosure belongs to the field of biotechnologies, and specifically relates to a polypeptide with an anti-*Mycobacterium tuberculosis* activity, and a preparation method and use thereof.

BACKGROUND

Antimicrobial peptides with diversified structures are found in mammalian species. Antimicrobial peptides are a group of natural host defensins secreted by the body's innate immune system. Antimicrobial peptides have a significant inhibiting and killing effect on microorganisms (bacteria, viruses, or the like) and even on tumor cells. BMAP-27 is a well-known peptide derived from bovine. BMAP-27 has an amphiphilic α-helical terminus produced from the cation $NH_2$. It has been proven that BMAP-27 exhibits potent killing activity against bacteria, fungi, viruses, and parasites. However, BMAP-27 has specified cytotoxicity and thus cannot be used as a drug. BMAP-18 is a truncated form of BMAP-27. Although BMAP-18 exhibits reduced toxicity to mammalian and insect cells, the toxicity and antibacterial effects of BMAP-18 are still unsatisfactory.

Tuberculosis (TB) is a zoonotic disease that is epidemic worldwide and continuously endangers human health and life. Globally, TB remains one of the top 10 causes of death in humans. The global number of TB deaths increased from 1.4 million in 2019 to 1.5 million in 2020, and further to 1.6 million in 2021. The number of patients with multidrug-resistant/rifampicin-resistant TB was 437,000 in 2020 and increased to 450,000 in 2021. Because drugs commonly used for treating TB, such as ethambutol, isoniazid, and rifampicin, have specified drug toxicity, easily cause hepatotoxicity and drug resistance, and exhibit unstable treatment effects, TB still poses a huge threat and damage to human safety and the development of animal husbandry.

TB pathogens include *Mycobacterium tuberculosis* or the like. There is a lack of drugs with small side effects and excellent anti-*Mycobacterium tuberculosis* effects in the prior art.

SUMMARY

An objective of the present disclosure is to provide a polypeptide with a low cytotoxicity and an excellent anti-*Mycobacterium tuberculosis* effect.

The objective of the present disclosure is allowed through the following technical solutions:

The present disclosure provides a polypeptide with an anti-*Mycobacterium tuberculosis* activity and having the sequence shown in SEQ ID NO: 3, where a structural formula of the polypeptide is as follows:

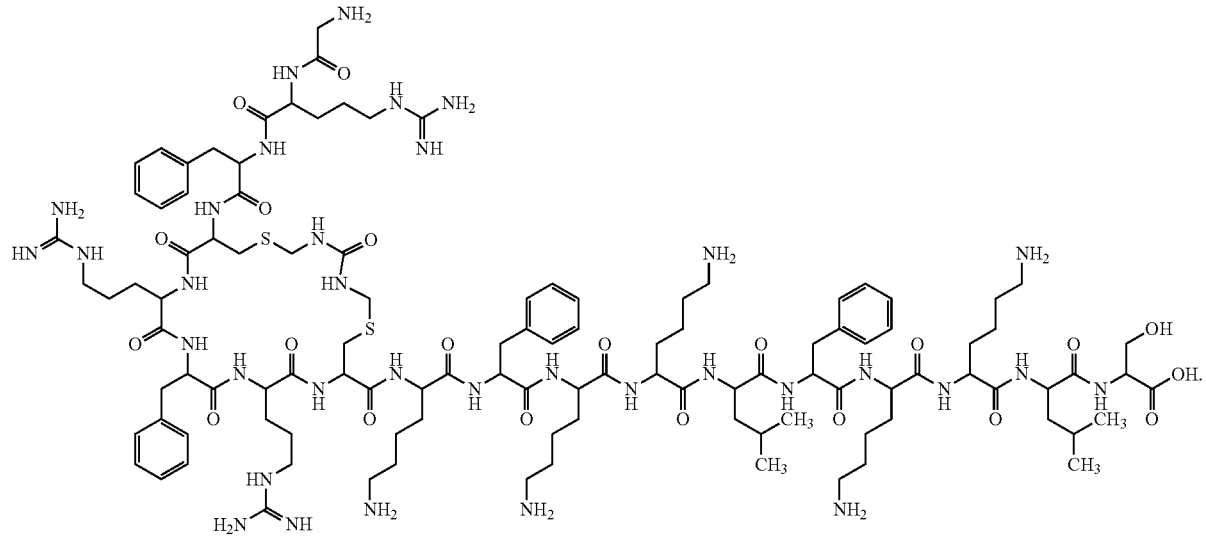

The present disclosure also provides a preparation method of the polypeptide, including the following steps:
(1) preparing a straight-chain polypeptide with a sequence shown in SEQ ID NO: 1; and
(2) allowing sulfhydryl groups of two cysteine residues in the straight-chain polypeptide to undergo a dehydration-condensation reaction with dimethylolurea to obtain the polypeptide.

In the present disclosure, a molar ratio of the straight-chain polypeptide to the dimethylolurea is 1:(8-12).

In the present disclosure, in the step (2), the straight-chain polypeptide and the dimethylolurea are dissolved in a solvent separately, and then mixed to allow the dehydration-condensation reaction.

In the present disclosure, a solvent for the straight-chain polypeptide is one of a mixed solution of trifluoroacetic acid (TFA) and guanidine hydrochloride, an aqueous urea solution, acetonitrile, and phosphate buffered saline (PBS); and a solvent for the dimethylolurea is one of water, acetonitrile, methanol, and N,N-dimethylformamide (DMF).

In the present disclosure, a concentration of the aqueous urea solution is 4 mol/L to 8 mol/L.

In the present disclosure, a concentration of the straight-chain polypeptide in the solvent is 1 mmol/L to 8 mmol/L, and a concentration of the dimethylolurea in the solvent is 18 mmol/L to 80 mmol/L.

In the present disclosure, during the reaction in the step (2), an acid reaction regulator is added; the acid reaction regulator is TFA; and a volume ratio of a solution of the straight-chain polypeptide to the acid reaction regulator is 1:1 to 1:3.

In the present disclosure, the reaction in the step (2) is conducted at 0° C. to 40° C. for 0 min to 10 min.

The present disclosure also provides a use of the polypeptide in preparation of an anti-*Mycobacterium tuberculosis* drug.

The polypeptide SAH1 of the present disclosure has an anti-*Mycobacterium tuberculosis* activity, and has the following advantages over the polypeptide BMAP-18 without modification: (1) Safety and few side effects: SAH1 exhibits a significantly-lower cytotoxicity than BMAP-18 to mouse macrophages. A cytotoxicity $IC_{50}$ value of SAH1 is 300 μM and a cytotoxicity $IC_{50}$ value of BMAP-18 is 150 μM. Therefore, the safety of SAH1 is significantly improved. (2) Improved anti-*Mycobacterium tuberculosis* effect: SAH1 can exhibit a strong anti-BCG bacterial infection effect at a concentration of 12.5 μM in the minimum inhibitory concentration (MIC) test. However, under the same conditions, a MIC of BMAP-18 is 300 μM, and an antibacterial ability of BMAP-18 is merely one twenty-fourth of an antibacterial ability of SAH1. Under a scanning electron microscope, it is also intuitively observed that the antibacterial ability of SAH1 is significantly improved compared with BMAP-18. (3) Strong anti-protease hydrolysis ability: After BMAP-18 is added to trypsin at a concentration of 5 μg/mL, BMAP-18 is completely hydrolyzed at 30 min. However, when SAH1 is placed in the same environment, 45.89% of SAH1 is still not hydrolyzed at 30 min, and 30.21% of SAH1 can still be left at 1 h. The polypeptide SAH1 is an antimicrobial peptide, which can play a disease-treating role while avoiding drug resistance and side effects through a unique action mode in the post-antibiotic era. Therefore, the polypeptide SAH1 has a very promising application prospect and a great research value.

BRIEF DESCRIPTION OF THE DRAWINGS

FIG. 8A is for a negative control, FIG. 8B is for BCG treated with BMAP-18, and FIG. 8C is for BCG treated with SAH1;

DETAILED DESCRIPTION OF THE EMBODIMENT

The BCG bacteria in the present application are attenuated *Mycobacterium bovis*, which has an ATCC number of bio-77983 and is purchased from the China Institute of Veterinary Drug Control.

The technical solutions of the present disclosure are described in detail below in conjunction with the accompanying drawings, but the protection scope of the present disclosure is not limited to the following examples.

Example 1 Screening and Preparation of the Polypeptide SAH1

1. Screening of the Polypeptide SAH1

Figure 1:
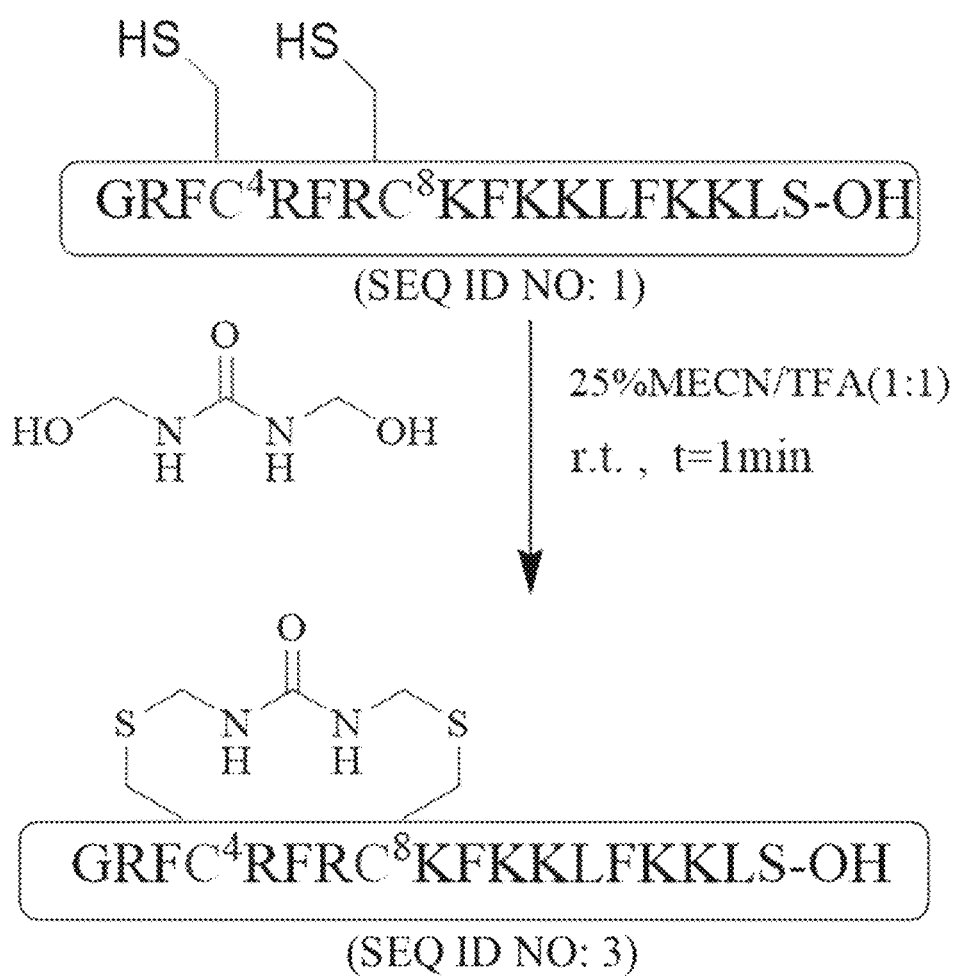
FIG. 1 shows a reaction principle for the preparation of the polypeptide SAH1.

A sequence of BMAP-18 (from N-terminus to C-terminus) was as follows: G-R-F-K-R-F-R-K-K-F-K-K-L-F-K-K-L-S-OH (Gly-Arg-Phe-Lys-Arg-Phe-Arg-Lys-Lys-Phe-Lys-Lys-Leu-Phe-Lys-Lys-Leu-Ser-OH) (SEQ ID NO: 2). BMAP-18 was modified through a point mutation of an amino acid at any position or a point mutation of amino acids at two random positions. It was finally found that the compound SAH1 exhibited both a reduced cytotoxicity and a highly-effective anti-*Mycobacterium tuberculosis* effect. As shown in FIG. 1, a specific modification method was as follows: Amino acids at positions 4 and 8 of BMAP-18 were mutated into cysteine to obtain G-R-F-C-R-F-R-C-K-F-K-K-L-F-K-K-L-S-OH (Gly-Arg-Phe-Cys-Arg-Phe-Arg-Cys-Lys-Phe-Lys-Lys-Leu-Phe-Lys-Lys-Leu-Ser-OH) (SEQ ID NO: 1), and then the mutant was subjected to a dehydration-condensation reaction with dimethylolurea to produce a cyclic peptide with the following structure:

(SEQ ID NO: 3)

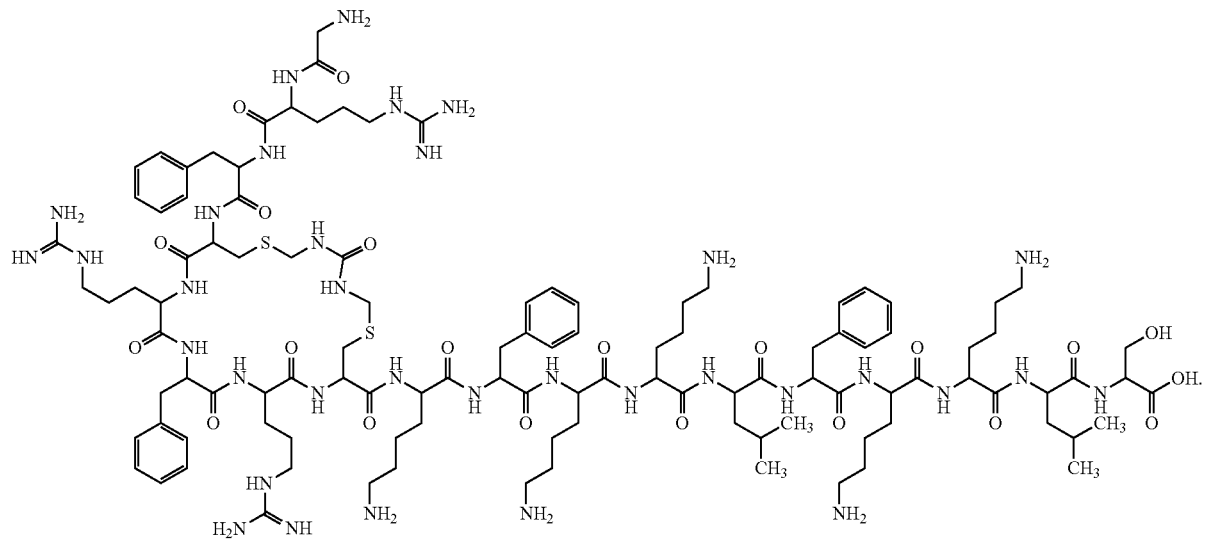

2. Preparation of the Polypeptide SAH1

(1) Preparation of a Straight-Chain Polypeptide GRFC⁴RFRC⁸KFKKLFKKLS-OH (SEQ ID NO: 1)

The Fmoc solid-phase synthesis was adopted to synthesize the polypeptide: GRFC$^4$RFRC$^8$KFKKLFKKLS-OH (from N-terminus to C-terminus) (SEQ ID NO: 1).

Coupling of a first amino acid: 0.2 mmol of a Wang resin was weighed and added to a solid-phase reaction column with xacin, washed with DMF 2 times, and then swelled with DMF for 30 min. 383.4 mg (1 mmol) of Fmoc-Ser (tBu)-OH and 142.11 mg (1 mmol) of Oxyma (ethyl cyanoglyoxylate-2-oxime) were weighed and dissolved in DMF, and then 0.25 g (2 mmol) of N,N'-diisopropylcarbodiimide (DIC) was added to allow activation for 3 min to obtain a coupling solution. The coupling solution was then added to the resin swelled with DMF to allow a coupling reaction at room temperature for 1 h. An end point of the reaction was detected with ninhydrin. If the resin was colorless and transparent, the reaction was terminated. If the resin was colored, the reaction was extended by 1 h. At the end of the reaction, a reaction liquid was removed, and a resulting resin was washed with DMF three times and then subjected to Fmoc protective group removal as follows: A piperidine aqueous solution with a concentration of 20% was added to make the resin immersed, a resulting mixture was stirred with a glass rod to allow a reaction for 3 min, and then a resulting piperidine solution was removed. A resulting resin was washed with DMF 3 times, then a piperidine aqueous solution with a concentration of 20% was added once again to make the resin immersed, a reaction was conducted for 4 min, a resulting reaction liquid was removed, and a resulting resin was washed with DMF 3 times to 5 times.

A second protective amino acid was coupled according to the method of coupling of Fmoc-Ser (tBu)-OH.

With the above method, the remaining amino acids were coupled sequentially from C-terminus to N-terminus to finally obtain a polypeptide GRFC$^4$RFRC$^8$KFKKLFKKLS-OH (SEQ ID NO: 1) resin.

The polypeptide GRFC$^4$RFRC$^8$KFKKLFKKLS-OH (SEQ ID NO: 1) resin was washed with DMF 3 times, washed with dichloromethane (DCM) 2 times, vacuum-dried, and subjected to a cleavage reaction specifically as follows: A lysis buffer was added to allow a lysis reaction at room temperature for 1 h, a resulting resin was filtered out, and a resulting filtrate was collected. Then the cleavage was repeated once with a small amount of the lysis buffer. Filtrates produced after the two times of cleavage were combined and slowly added to glacial diethyl ether for precipitation, and a resulting system was centrifuged to obtain a precipitate and a supernatant. The supernatant was discarded, and the precipitate was dried under reduced pressure to obtain a crude straight-chain polypeptide GRFC$^4$RFRC$^8$KFKKLFKKLS-OH (SEQ ID NO: 1). The lysis buffer was a mixed solution of TFA, triisopropylsilane (TIS), and H$_2$O in a volume ratio of 95:2.5:2.5.

Figure 2:
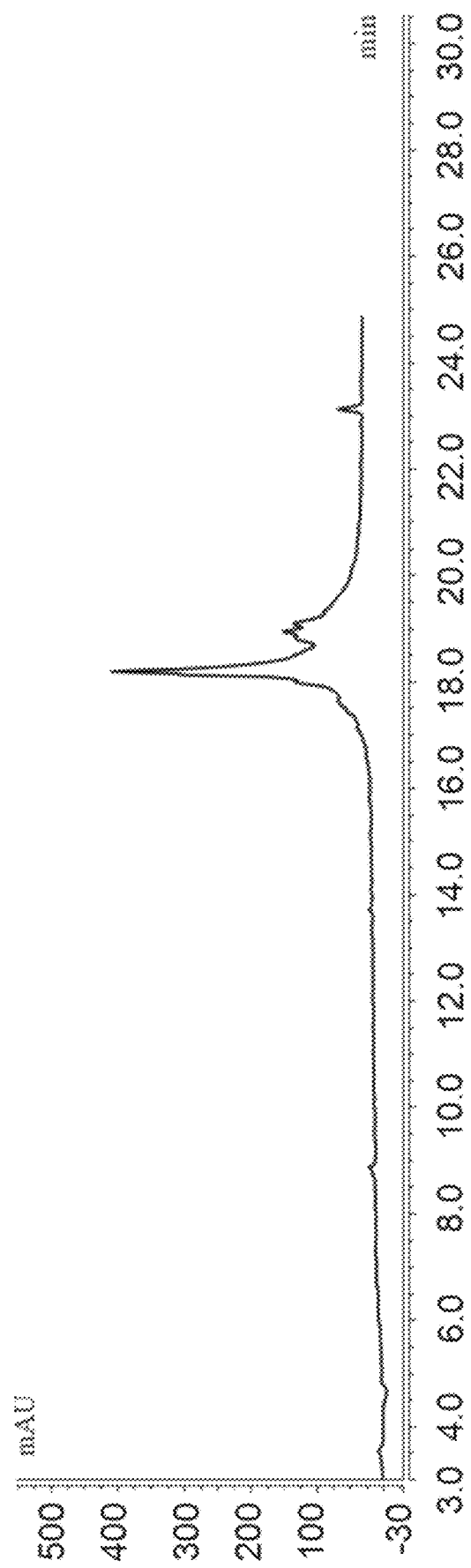
FIG. 2 shows a chromatography spectrum of the crude straight-chain polypeptide GRFC$^4$RFRC$^8$KFKKLFKKLS-OH (SEQ ID NO: 1)
Figure 3:
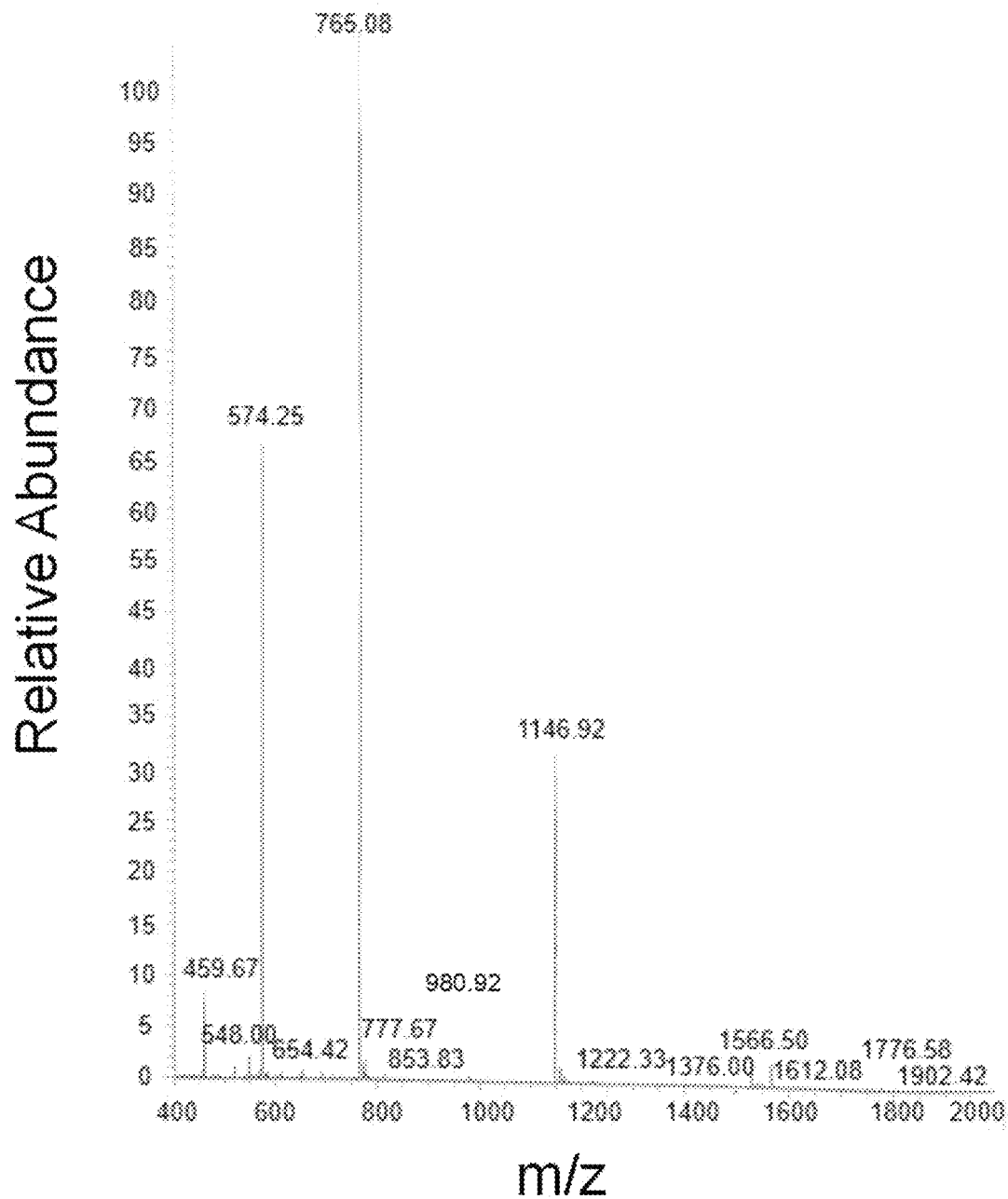
FIG. 3 is a mass spectrometry spectrum of the polypeptide GRFC$^4$RFRC$^8$KFKKLFKKLS-OH (SEQ ID NO: 1)

The crude straight-chain polypeptide GRFC$^4$RFRC$^8$KFKKLFKKLS-OH (SEQ ID NO: 1) was lyophilized as follows: The crude straight-chain polypeptide was frozen with liquid nitrogen into a solid, and then the solid was suspended in a lyophilizer for lyophilization to obtain a solid powder. The straight-chain polypeptide GRFC⁴RFRC⁸KFKKLFKKLS-OH (SEQ ID NO: 1) was identified by liquid chromatography-mass spectrometry (LC-MS). A corresponding chromatography spectrum was shown in FIG. 2, and a corresponding mass spectrometry spectrum was shown in FIG. 3. Mass spectrometry data were as follows: M=2292.3, found: 1147 $[M+2H^+]^{2+}$, 765.25 $[M+3H^+]^{3+}$, 574.33 $[M+4H^+]^{4+}$, 459.75 $[M+5H^+]^{5+}$.

A structural formula of the straight-chain polypeptide GRFC⁴RFRC⁸KFKKLFKKLS-OH (SEQ ID NO: 1) was as follows:

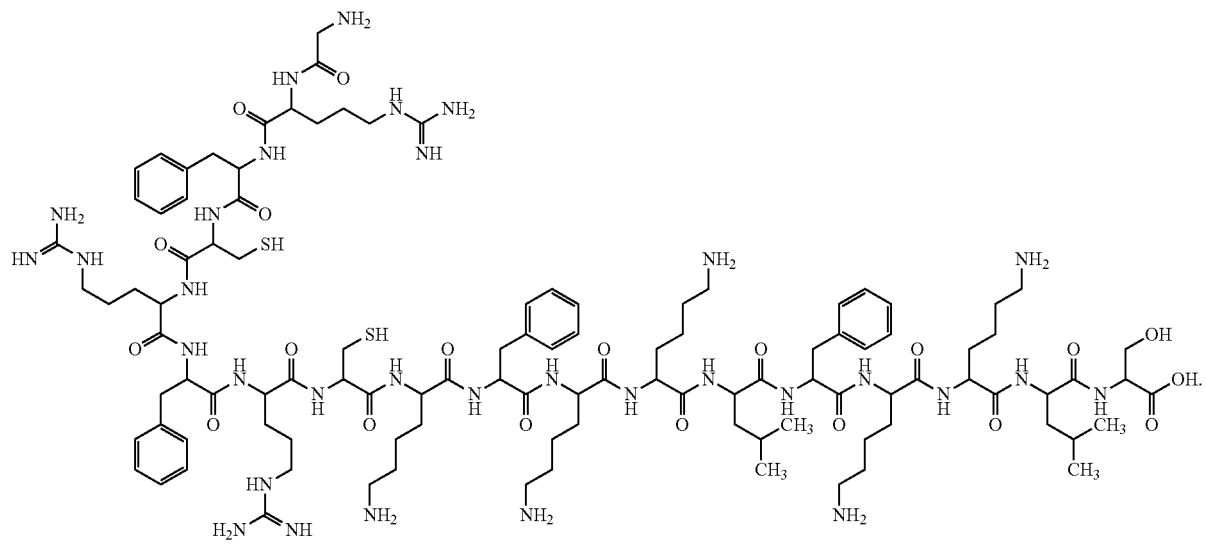

Chemical Formula: $C_{107}H_{174}N_{32}O_{20}S_2$

A sequence of the straight-chain polypeptide (SEQ ID NO: 1) was as follows: GRFCRFRCKFKKLFKKLS.

(2) Two cysteine residues in the straight-chain polypeptide were modified and stapled with dimethylolurea.

The crude straight-chain polypeptide GRFC⁴RFRC⁸KFKKLFKKLS-OH (SEQ ID NO: 1) was allowed to directly react with dimethylolurea under acidic conditions to obtain a stapled cyclic peptide, which reduced the operation processes, improved the production efficiency, and reduced the consumption of organic solvents. Specific steps were as follows:

Step 1: The crude straight-chain polypeptide GRFC⁴RFRC⁸KFKKLFKKLS-OH (SEQ ID NO: 1) was taken and dissolved in a mixed solution of TFA and guanidine hydrochloride in a volume ratio of 1:1 to obtain a 2 mmol/L polypeptide solution. Dimethylolurea was dissolved in water to obtain a 20 mmol/L dimethylolurea aqueous solution.

Step 2: At room temperature, anhydrous TFA was added to the 2 mmol/L polypeptide solution, then the 20 mmol/L dimethylolurea aqueous solution was added, and a reaction was conducted at room temperature for 1 min to obtain a crude dimethylolurea-modified polypeptide. The polypeptide solution, the anhydrous TFA, and the dimethylolurea aqueous solution were in a volume ratio of 1:1:1.

Figure 4:
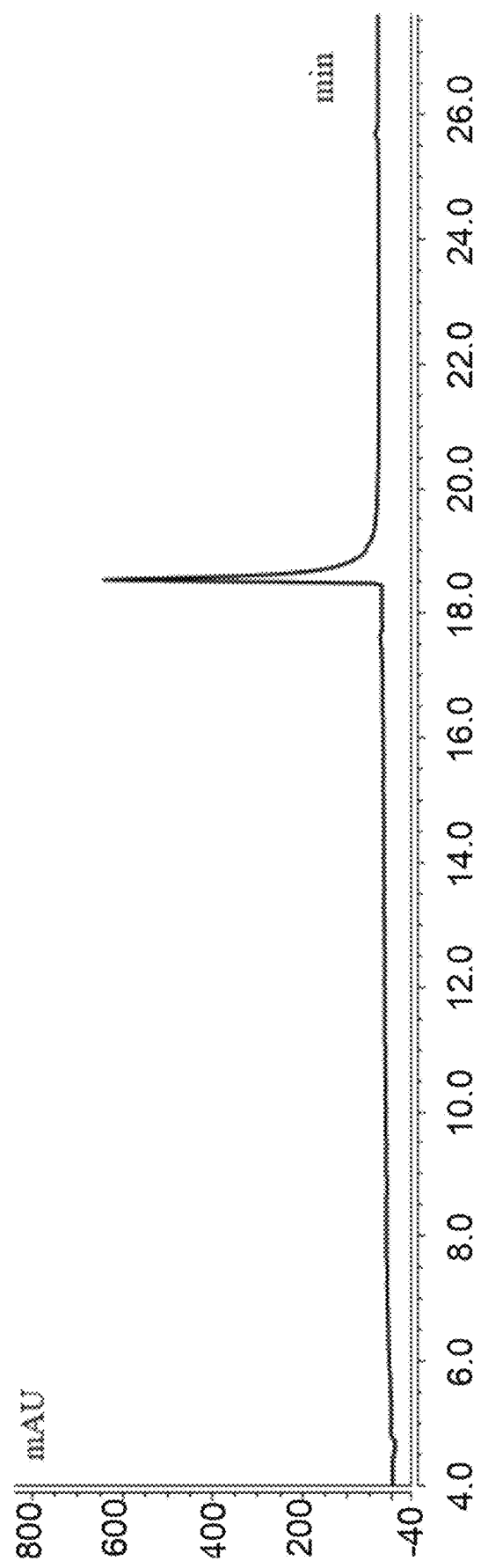
FIG. 4 is a preparative chromatography spectrum of a dimethylolurea-modified polypeptide.

Step 3: The crude dimethylolurea-modified polypeptide was purified by semi-preparative high-performance liquid chromatography under the following conditions: mobile phases: A: 0.1% (volume percentage concentration) TFA-containing $H_2O$, and B: 0.1% (volume percentage concentration) TFA-conating acetonitrile; an elution procedure: 0 min to 30 min: the mobile phase B: from 0% to 60%, with an increment of 2% of B per minute; a chromatographic column: Waters C18; a flow rate: 15 mL/min; and a detection wavelength: 214 nm. As shown in FIG. 4, the prepared dimethylolurea-modified polypeptide had a high purity.

Figure 5:
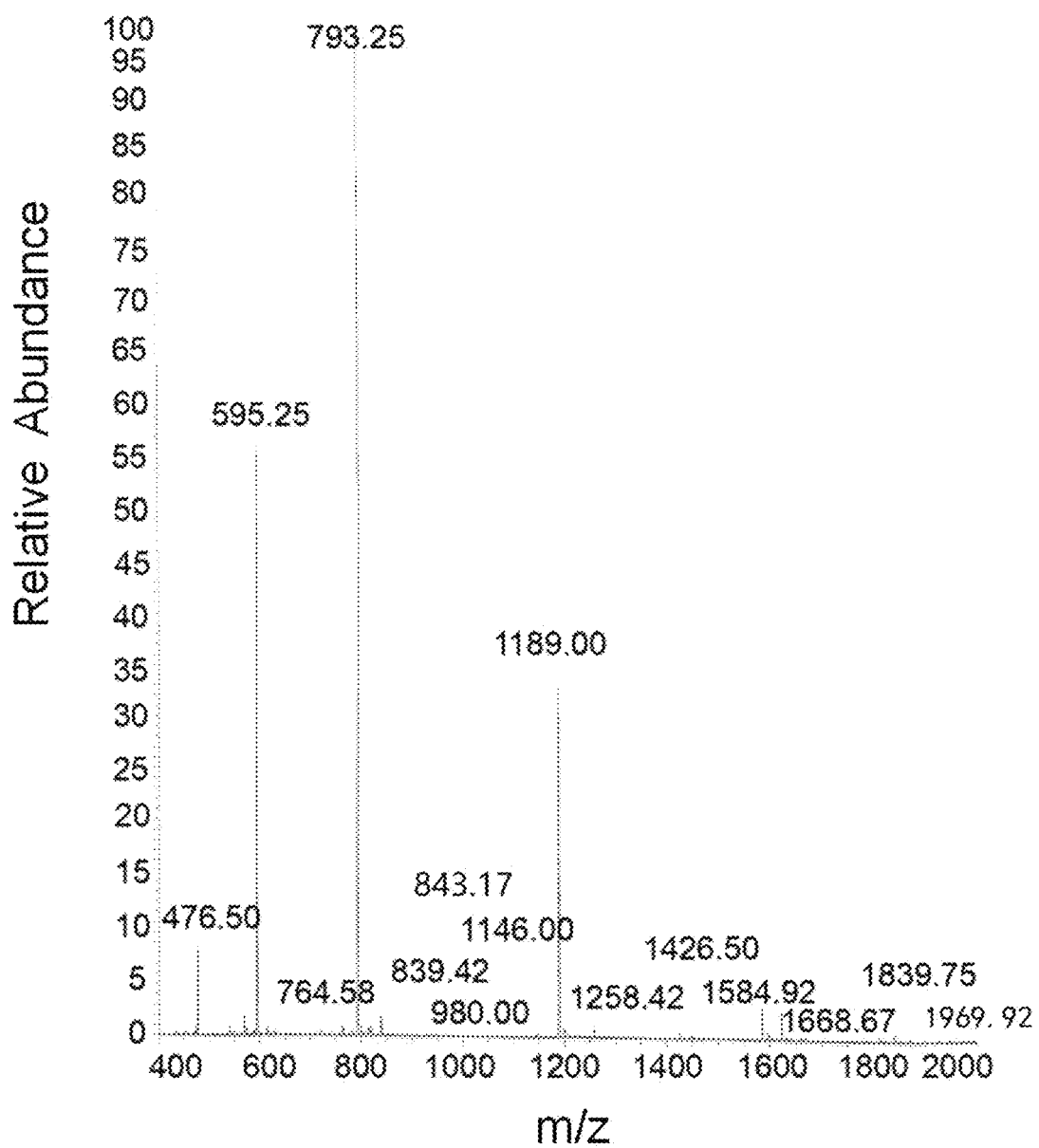
FIG. 5 is a mass spectrometry spectrum of a dimethylolurea-modified polypeptide.

The purified dimethylolurea-modified polypeptide was lyophilized as follows: The purified dimethylolurea-modified polypeptide was frozen with liquid nitrogen into a solid, and then the solid was suspended in a lyophilizer for lyophilization obtain a solid powder. The purified dimethylolurea-modified polypeptide was identified by mass spectrometry, as shown in FIG. 5. Mass spectrometry data were as follows: M=2376.9, found: 1188.92 $[M+2H^+]^{2+}$, 792.92 $[M+3H^+]^{3+}$, 595.00 $[M+4H^+]^{4+}$, 476.25 $[M+5H^+]^{5+}$.

A structural formula of the dimethylolurea-modified polypeptide was as follows:

(SEQ ID NO: 3)

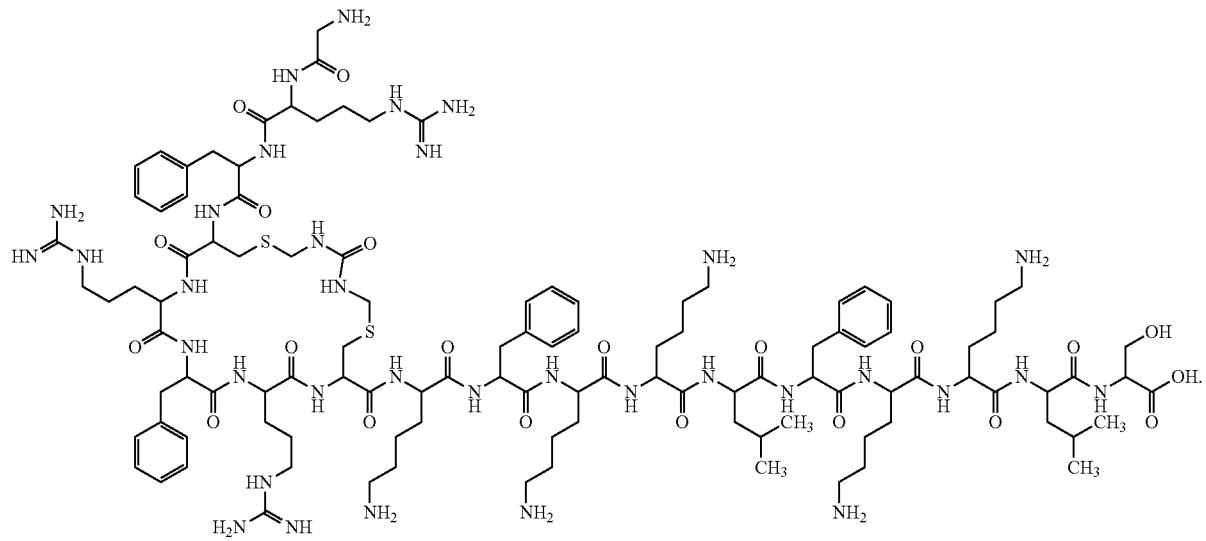 [SMILES: CC(C)CC(NC(=O)C(CCCCN)NC(=O)C(CCCCN)NC(=O)C(Cc1ccccc1)NC(=O)C(CC(C)C)NC(=O)C(CCCCN)NC(=O)C(CCCCN)NC(=O)C(Cc1ccccc1)NC(=O)C(CCCCN)NC(=O)C1CSCNC(=O)NCSCC(NC(=O)C(Cc2ccccc2)NC(=O)C(CCCNC(=N)N)NC(=O)CN)C(=O)NC(CCCNC(=N)N)C(=O)NC(Cc2ccccc2)C(=O)NC(CCCNC(=N)N)C(=O)N1)C(=O)NC(CO)C(=O)O]

The dimethylolurea-modified polypeptide was denoted as a polypeptide SAH1.

Example 2 Detection of Cell Viabilities of RAW264.7 Cells Treated with SAH1 and BMAP-18 by a CCK-8 Method The toxicities of SAH1 and BMAP-18 to RAW264.7 cells were determined by the CCK-8 method, namely, a WST (chemical name: 2-(2-methoxy-4-nitrophenyl)-3-(4-nitrophenyl)-5-(2,4-dithophenyl)-2H-tetrazolium monosodium salt) colorimetric test. A specific method was as follows: $1 \times 10^5$ RAW 264.7 cells were inoculated into each well of a 96-well plate, 100 μL of a polypeptide SAH1 aqueous solution serially diluted to a concentration of 3.125 μM to 200 μM was added to each test well, and the plate was incubated at 37° C. and 5% $CO_2$ for 24 h. A positive control well was set. The positive control well was the same as test wells except that the polypeptide SAH1 aqueous solution was replaced with a DMEM complete medium. A blank well was set. In the blank well, no cells were added, and only the DMEM complete medium was added. After the incubation, 10 μL of a CCK-8 reaction solution (Beijing Solarbio) was added to each well, and the plate was further incubated at 37° C. for 2 h. Finally, the absorbance at 450 nm was detected with a microplate reader (Synersymx, Biotek) to determine a cell viability. According to the formula: cell viability=(absorbance of a test well−absorbance of a blank well)/(absorbance of a positive control well−absorbance of a blank well) * 100%, a cell viability relative to the positive control well was calculated.

In addition, the same method was used to detect viabilities of cells treated with BMAP-18 aqueous solutions serially diluted to concentrations of 3.125 μM to 200 μM.

Figure 6:
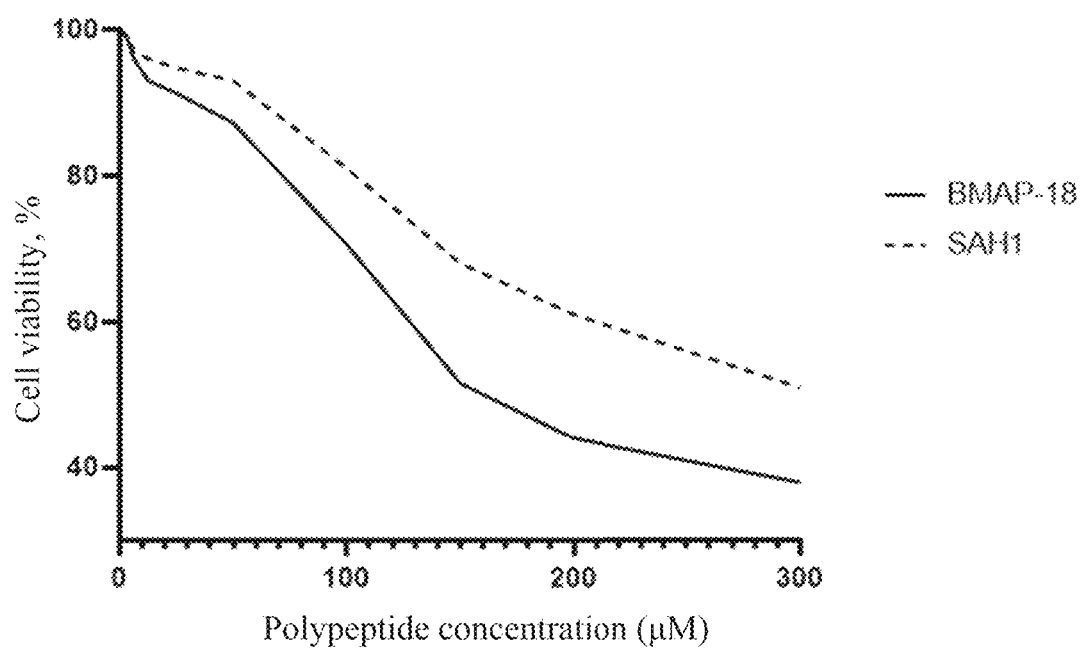
FIG. 6 shows cell viabilities of RAW264.7 cells treated with SAH1 and BMAP-18 at each concentration, where an x-coordinate represents a concentration in μM, and a y-coordinate represents a cell viability in %.

It can be seen from FIG. 6 that SAH1 exhibits a significantly lower cytotoxicity than BMAP-18 at each concentration gradient, SAH1 does not exhibit a significant cytotoxicity to RAW264.7 cells (cell viability: higher than 90%) at a concentration of 50 μM or lower, and BMAP-18 does not exhibit a significant cytotoxicity to RAW264.7 cells (cell viability: higher than 90%) at a concentration of 25 μM or lower.

Example 3 Fitting Results of $IC_{50}$ Values of SAH1 and BMAP-18 for RAW264.7 Cells $1 \times 10^5$ RAW 264.7 cells were inoculated into each well of a 96-well plate, 100 μL of a polypeptide SAH1 aqueous solution serially diluted to a concentration of 3.125 μM to 200 μM was added to each test well, and the plate was incubated at 37° C. and 5% $CO_2$ for 24 h. A positive control well was set. The positive control well was the same as test wells except that the polypeptide SAH1 aqueous solution was replaced with a DMEM complete medium. After the incubation, 10 μL of a CCK-8 reaction solution (Beijing Solarbio) was added to each well, and the plate was further incubated at 37° C. for 2 h. Finally, the absorbance at 450 nm was detected with a microplate reader (Synersymx, Biotek). An OD value of the positive control well was BO, an OD value of a test well in which an antimicrobial peptide was added was B, and B/BO was called an inhibition rate. A concentration of an antimicrobial peptide corresponding to an inhibition rate of 50% was called $IC_{50}$. The lower the $IC_{50}$ value, the stronger the cytotoxicity of the antimicrobial peptide. With a concentration of an antimicrobial peptide as an x-coordinate and an inhibition rate as a y-coordinate, a line chart was plotted, and $IC_{50}$ was obtained through fitting.

$IC_{50}$ of BMAP-18 for RAW 264.7 cells was obtained by the same method.

Figure 7:
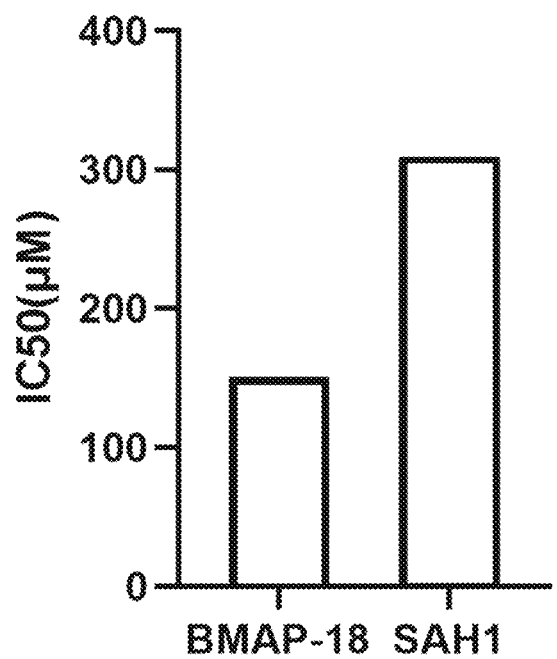
FIG. 7 shows fitting results of $IC_{50}$ values of SAH1 and BMAP-18 for RAW264.7 cells.

It can be seen from FIG. 7 that $IC_{50}$ values of SAH1 and BMAP-18 for RAW 264.7 cells are 300 μM and 150 μM, respectively, indicating that SAH1 has a lower cytotoxicity than BMAP-18.

Example 4 Determination of an Ability of SAH1 to Inhibit the Growth of BCG Bacteria by MIC Assay An antibacterial effect of SAH1 at each concentration on BCG bacteria was investigated. SAH1 was serially diluted in a range of 6.25 μM to 3,200 μM with a $7H_9$ medium as a solvent to obtain SAH1 solutions with different concentrations. BMAP-18 was serially diluted in a range of 6.25 μM to 3,200 μM with a $7H_9$ medium as a solvent to obtain BMAP-18 solutions with different concentrations. Rifampicin, isoniazid, and ethambutol each were serially diluted in a range of 25 μM to 12,800 μM with a 7H9 medium as a solvent to obtain rifampicin solutions, isoniazid solutions, and ethambutol solutions each with different concentrations. A solution of each drug was filtered through a 0.22 μm filter to remove bacteria.

An SAH1 test group was set as follows: 0.1 mL of an SAH1 solution at each concentration was added to a centrifuge tube, and then 0.1 mL of BCG bacteria at $1.5 \times 10^7$ cfu/mL was added. A positive control was set as follows: the positive control was the same as the SAH1 test group except that a 7H9 medium was used instead of an SAH1 solution. A negative control was set as follows: the negative control was the same as the SAH1 test group except that the same volume of ultrapure water was used instead of BCG bacteria. In addition, a BMAP-18 test group, a rifampicin test group, an isoniazid test group, and an ethambutol test group were set. These test groups were the same as the SAH1 test group except that BMAP-18, rifampicin, isoniazid, or ethambutol was used instead of the SAH1 solution. After each centrifuge tube was incubated at 37° C. for 7 d, a resazurin indicator was added to allow an action for 2 d, and a color change was observed. After the two days of the action: If a medium was blue, it meant that there were no bacteria in a corresponding centrifuge tube, indicating that a drug at a corresponding concentration had an antibacterial effect. If a medium was purple and red, it meant that there were viable bacteria in a corresponding centrifuge tube, indicating that a drug at a corresponding concentration had no antibacterial effect.

Results were shown in Table 1. MIC of SAH1 was 12.5 μM, which was significantly lower than MICs of BMAP-18, rifampicin, isoniazid, and ethambutol, indicating that an antibacterial ability of SAH1 was significantly improved compared with BMAP-18.

TABLE 1

| MIC of each drug | |
| --- | --- |
| Drug | MIC |
| SAH1 | 12.5 μM |
| BMAP-18 | 300 μM |
| Rifampicin | 400 μM |
| Isoniazid | 800 μM |
| Ethambutol | 800 μM |

Example 5 Observation of Impacts of SAH1 and BMAP-18 on the Integrity of a Cell Membrane of BCG by a Scanning Electron Microscope BCG bacteria growing to a logarithmic phase were collected, suspended in a fresh 7H9 medium, and adjusted to $OD_{600}$ nm of 0.5. Then SAH1 at a final concentration of 12.5 μM and BMAP-18 at a final concentration of 300 μM were added separately. In a negative control, sterile $ddH_2O$ was added instead of an antimicrobial peptide. The cells were cultivated at 37° C. for 1 h. At the end of cultivation, bacterial cells were collected through centrifugation, washed 3 times with PBS (0.1 M, pH 7.0), resuspended with 2.5% glutaraldehyde, thoroughly dispersed, and placed at 4° C. overnight to fix bacteria. A resulting bacterial pellet was washed 3 times with PBS (0.1 M, pH 7.0), a 1% $O_sO_4$ aqueous solution was added to allow an action for 1 h, and then the bacterial pellet was subjected to centrifugal washing 3 times with PBS (0.1 M, pH 7.0). The dehydration was conducted with ethanol at different concentrations (30%, 50%, 70%, 80%, 90%, and 100%) for 15 min to 20 min each time. A resulting product was then treated with a mixture of ethanol and isoamyl acetate (v:v=1:1) for 30 min, then treated with pure isoamyl acetate for about 1 h, dehydrated with liquid carbon dioxide in a critical point dryer, and then coated with gold at 45 mA for 2 min. Finally, a treated sample was observed under a scanning electron microscope.

Figure 8A:
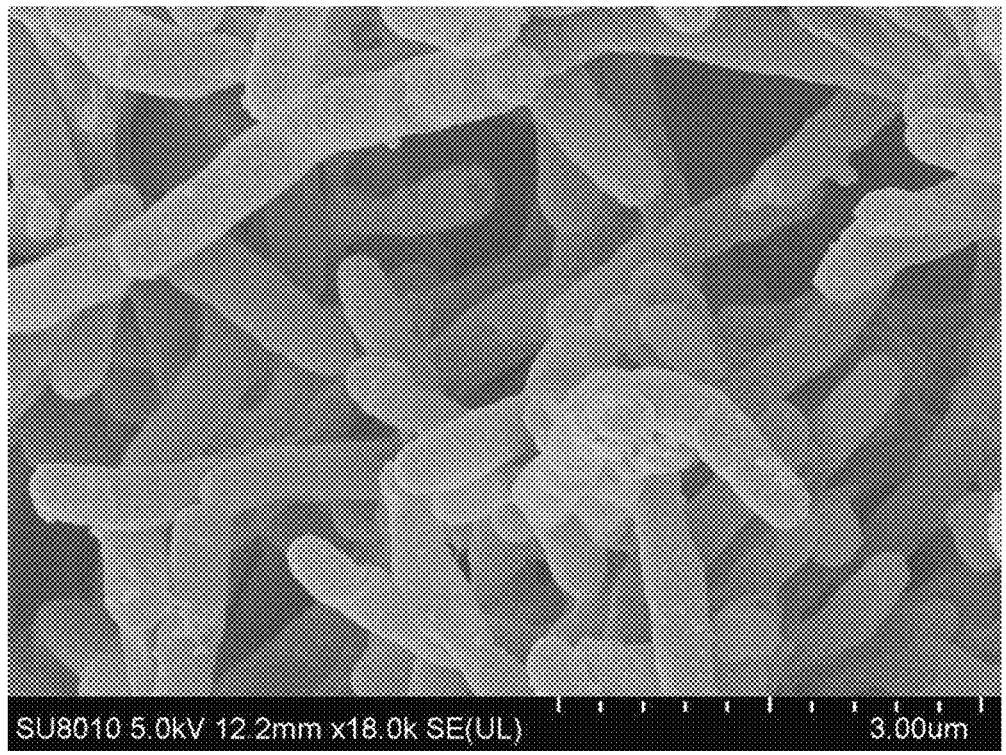
FIGS. 8A-8C show impacts of SAH1 and BMAP-18 on the integrity of cell membranes of BCG observed under a scanning electron microscope, where
Figure 8B:
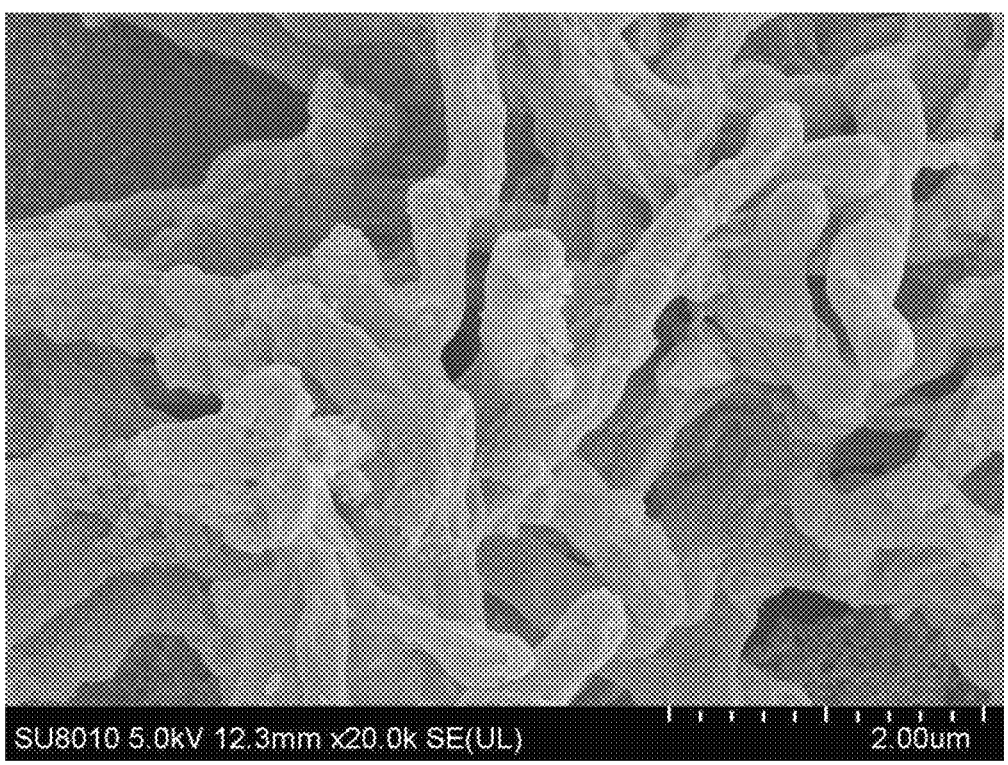
Figure 8C:

It can be seen from FIGS. 8A-8C that SAH1 exhibits a significantly-higher damage degree than BMAP-18 to the cell membrane and cell of BCG at MIC, and when a cell membrane of Mycobacteria is damaged, contents leak to cause the atrophy and even death of bacteria.

Example 6 Observation of an Impact of SAH1 on a Cell Membrane and an Intracellular Structure of BCG by a Transmission Electron Microscope BCG at a logarithmic phase was treated according to the method in Example 5. BCG was pre-dehydrated with ethanol at different concentration gradients, then treated with anhydrous acetone for 20 min, then treated with a mixed solution of anhydrous acetone and an EPON812 resin (V/V=1:1) at room temperature for 1 h, and then treated with a mixed solution of anhydrous acetone and an EPON812 resin (V/V=1:3) at room temperature for 3 h. Then, a bacterial sample was soaked overnight in an EPON812 resin twice. A treated sample was placed in an EP tube with the EPON812 resin and treated at 70° C. for 9 h or more.

Sectioning was conducted with an ultramicrotome, and staining was conducted with uranyl acetate and alkaline lead citrate successively for 5 min to 10 min. Finally, a bacterial sample was observed under a transmission electron microscope. In addition, a negative control was set. A specific treatment method for the negative control was the same as the treatment method for each sample except that BCG at a logarithmic phase was not treated with any antimicrobial substance.

Figure 9A:
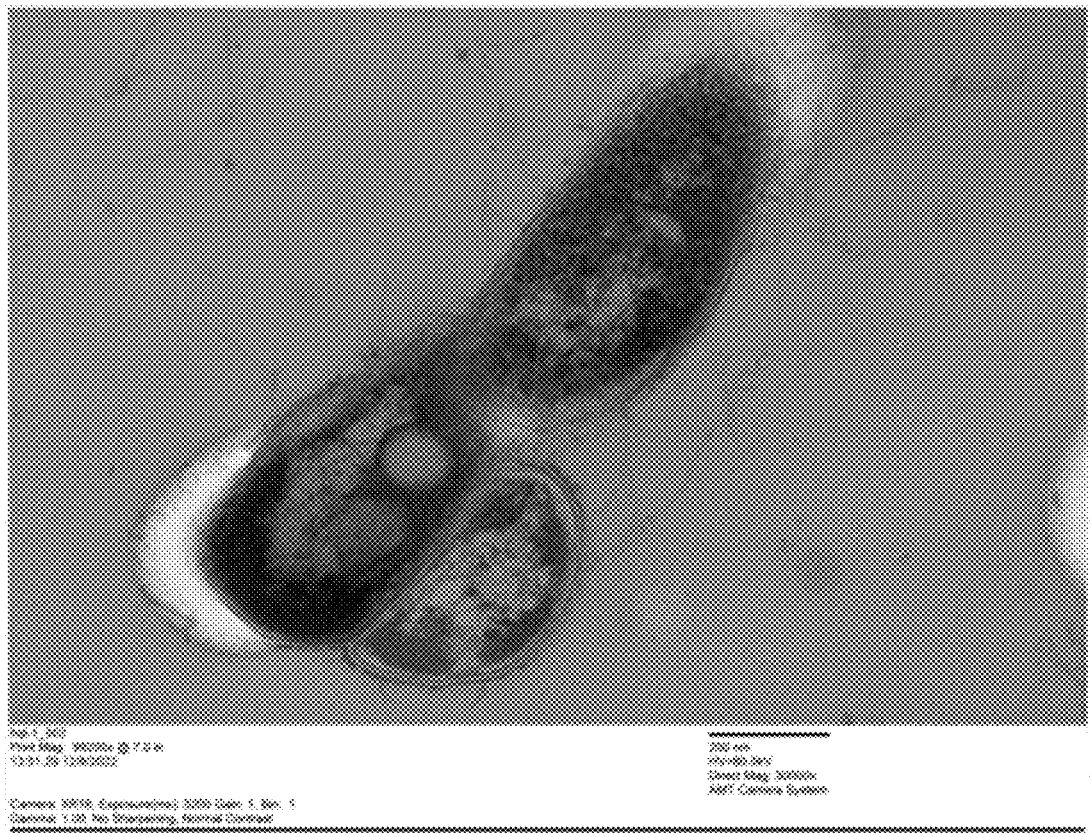
FIGS. 9A-9B show an impact of SAH1 on a cell membrane and an intracellular structure of BCG observed under a transmission electron microscope.
Figure 9B:
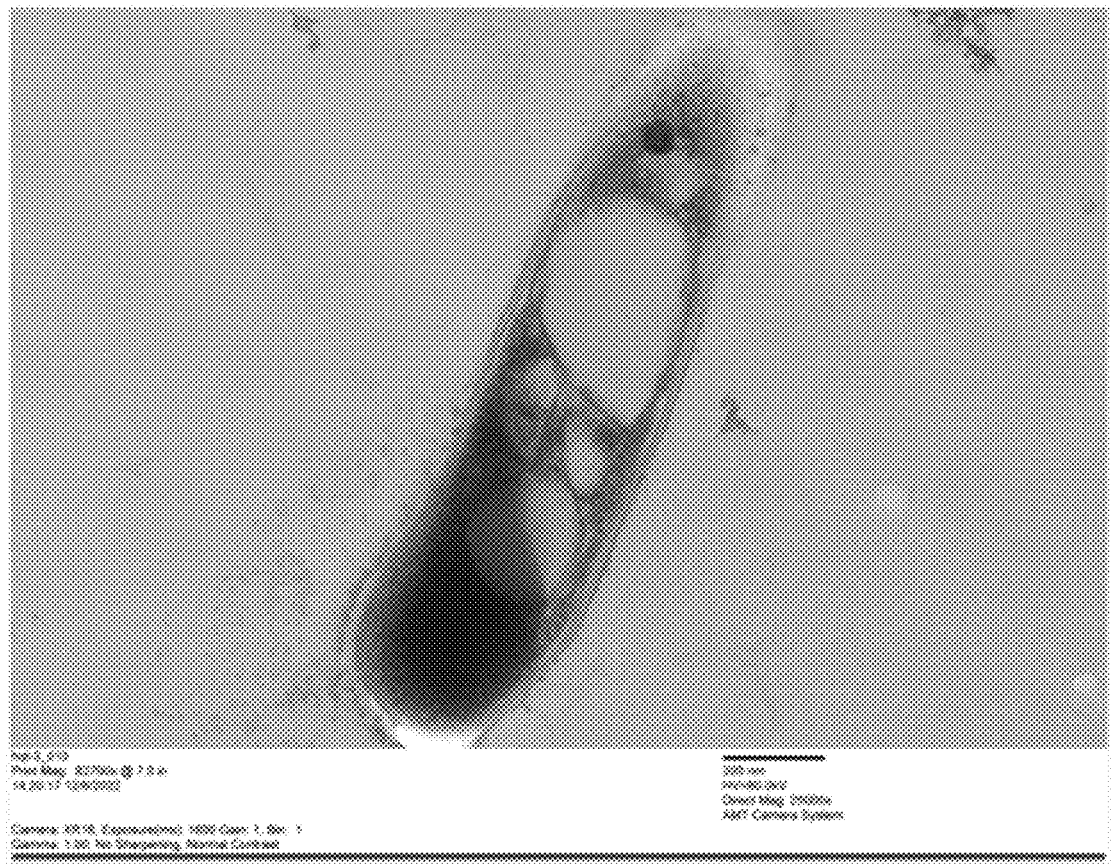
Figure 10A:
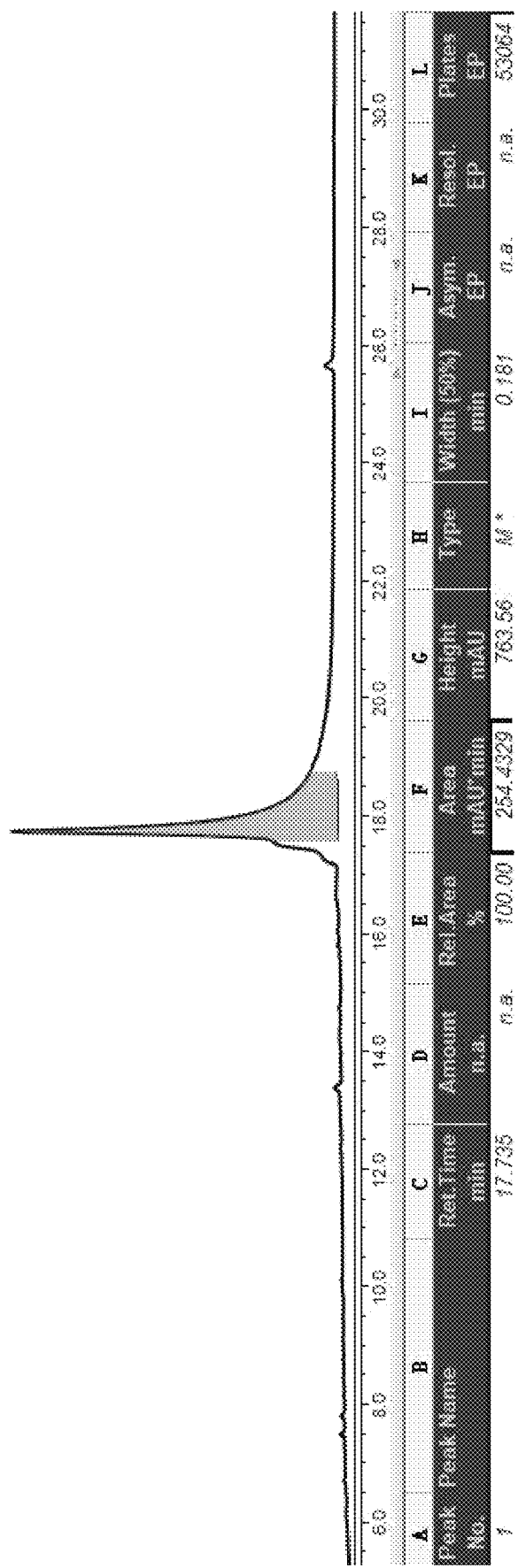
FIGS. 10A-10C show reverse phase-high performance liquid chromatography (RP-HPLC) spectra illustrating polypeptide residues of BMAP-18 in a trypsin (5 μg/mL) environment at different time points, where a reaction time of FIG. 10A is 0 min, a reaction time of FIG. 10B is 15 min, and a reaction time of FIG. 10C is 30 min.
Figure 10B:
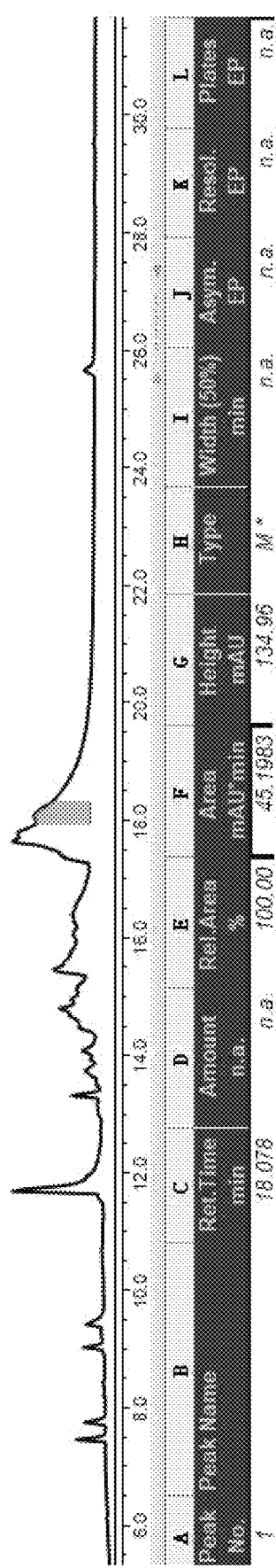
Figure 10C:
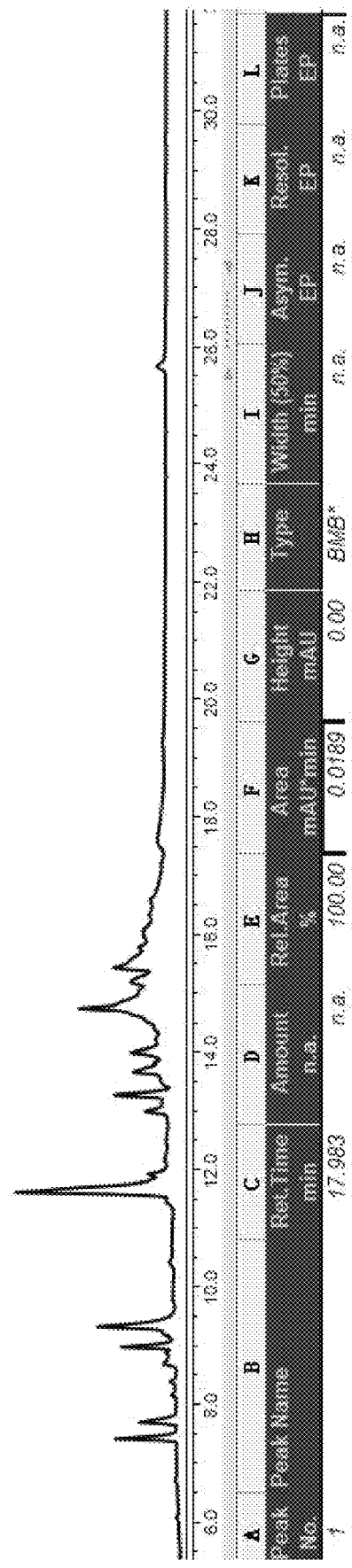
Figures 11A, 11B:
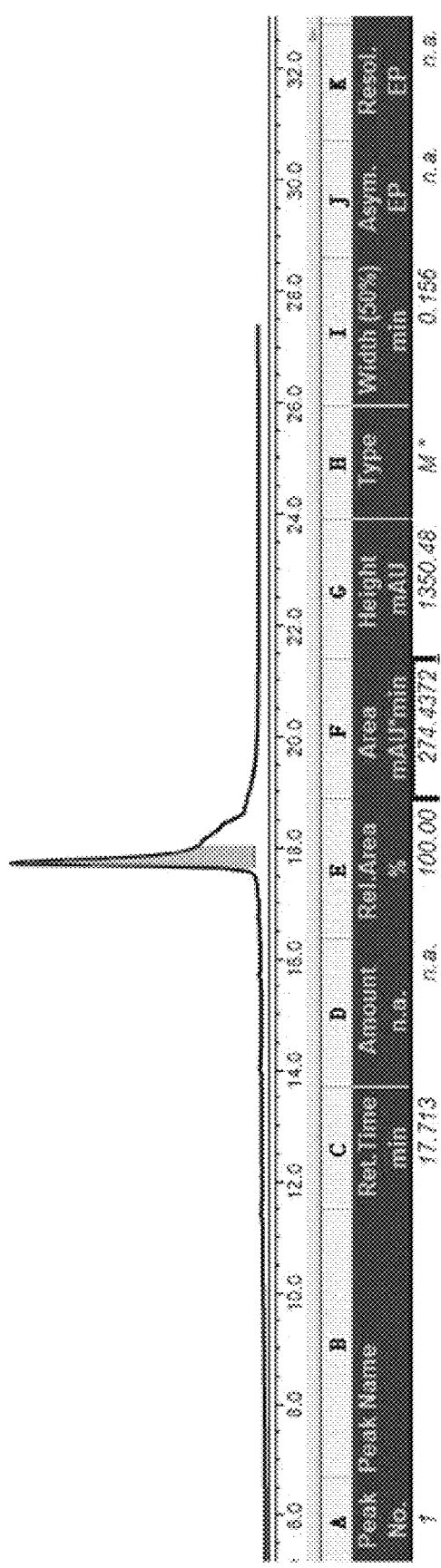
FIGS. 11A-11D show RP-HPLC spectra illustrating polypeptide residues of SAH1 under an action of trypsin (5 μg/mL) at different time points, where a reaction time of FIG. 11A is 0 min, a reaction time of FIG. 11B is 15 min, a reaction time of FIG. 11C is 30 min, and a reaction time of FIG. 11D is 60 min.
Figure 11C:
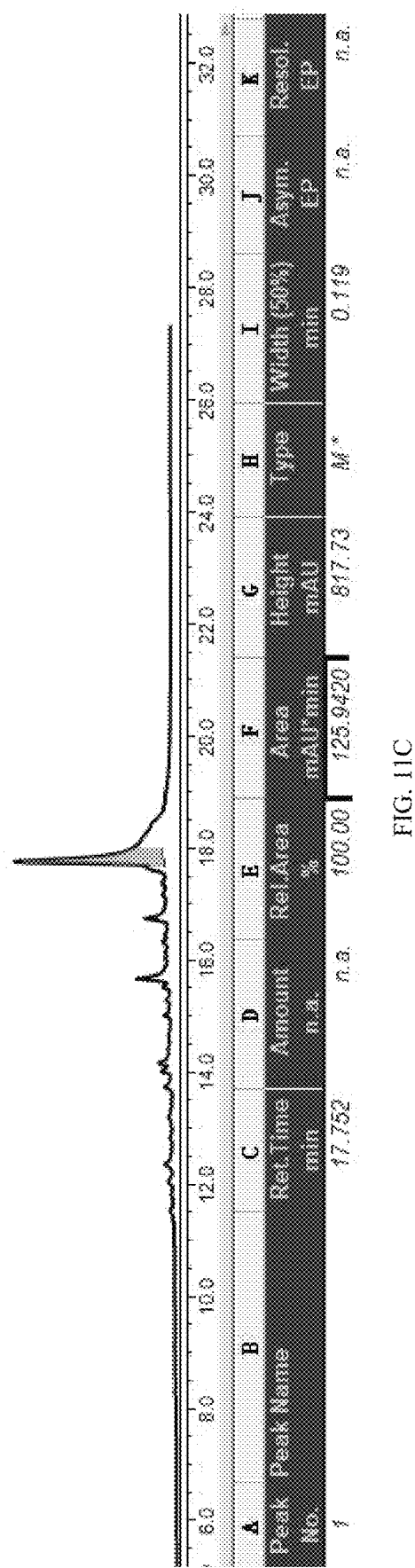
Figure 11D:
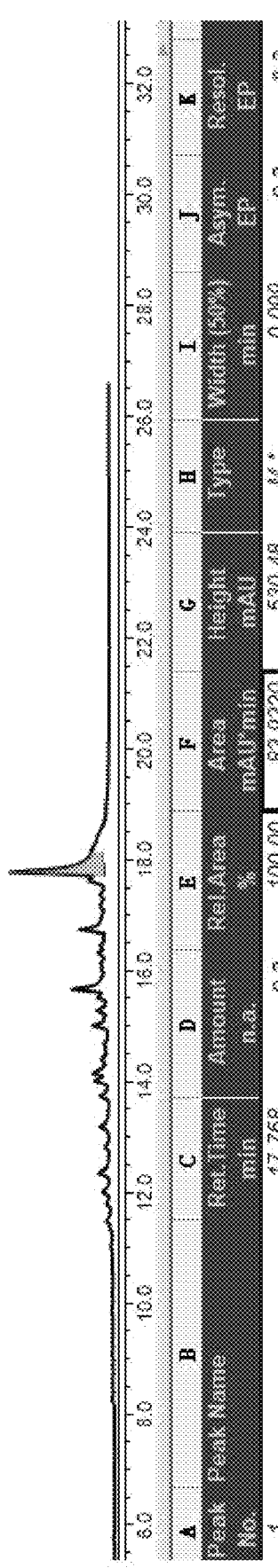

It can be seen from FIGS. 9A-9B that contents of BCG cells treated with SAH1 are largely missed, resulting in cavities and bacterial death.

Example 7 Determination of Abilities of SAH1 and BMAP-18 to Resist Protease Hydrolysis by Trypsin Assay A 4 mg/mL SAH1 solution and a 10 μg/mL trypsin solution each were prepared with PBS (pH 7.4) as a solvent. 250 μL of the trypsin solution was added to 250 μL of the SAH1 solution, and a reaction was conducted in an ice bath. A sample was collected at different time points after the reaction to determine the decomposition of SAH1 by RP-HPLC. RP-HPLC conditions were as follows: A C18 reversed-phase Bio-Rad analytical column was adopted: 250× 4 mm, a pore size: 30 nm, and a particle size: 7 μm. At 0 min to 40 min, linear gradient elution was conducted with 10% to 90% acetonitrile aqueous solutions, with 0.1% TFA (w/v) in both acetonitrile and water. A flow rate was 1.2 mL/min.

In addition, with the same method as above, the SAH1 aqueous solution was replaced with a 4 mg/mL BMAP-18 aqueous solution to detect the hydrolysis of BMAP-18 by trypsin.

After SAH1 reacted with trypsin for different time periods, a residual polypeptide amount was determined by RP-HPLC. According to Table 2, FIGS. 10A-10C, and FIGS. 11A-11D: Residual polypeptide proportions of SAH1 treated with trypsin for 15 min, 30 min, and 60 min were 67.59%, 45.89%, and 30.21%, respectively. After BMAP-18 was treated with trypsin for 15 min, a residual polypeptide proportion was merely 17.76%. After BMAP-18 was treated with trypsin for 30 min, the polypeptide was almost completely hydrolyzed. It can be known that an anti-protease hydrolysis ability of SAH1 is significantly enhanced compared with BMAP-18.

TABLE 2

| Polypeptide residues of SAH1 and BMAP-18 under the action of trypsin | | | |
| --- | --- | --- | --- |
| Antimicrobial peptide name | Reaction time | Peak area | Polypeptide residue |
| BMAP-18 | 0 min | 254.43 | 100% |
| | 15 min | 45.20 | 17.76% |
| | 30 min | 0.02 | 0.01% |
| SAH1 | 0 min | 274.44 | 100% |
| | 15 min | 185.49 | 67.59% |
| | 30 min | 125.94 | 45.89% |
| | 60 min | 82.92 | 30.21% |

Notes: A calculation method of a polypeptide residue in Table 2 is as follows: With an HPLC peak area at the initial reaction time of O min as 100%, a polypeptide residue is calculated according to the following formula: RP-HPLC peak area of a polypeptide residue/RP-HPLC peak area of an initial polypeptide * 100%.

What is claimed is:

1. A polypeptide with an anti-*Mycobacterium tuberculosis* activity and having the sequence according to SEQ ID NO: 3, wherein the SEQ ID NO: 3 has a structural formula of the polypeptide as follows:

[Chemical structural formula of the polypeptide]

2. A method of preparing the polypeptide according to claim 1, comprising the following steps:
   (1) synthesizing a straight-chain polypeptide according to SEQ ID NO: 1 by Fmoc solid-phase coupling; and
   (2) dissolving the straight-chain polypeptide and dimethylolurea in a solvent separately, and then mixing to allow sulfhydryl groups of two cysteine residues in the straight-chain polypeptide to undergo a dehydration-condensation reaction with dimethylolurea to obtain the polypeptide.

3. The method according to claim 2, wherein a molar ratio of the straight-chain polypeptide to the dimethylolurea is 1:8 to 1:12.

4. The method according to claim 3, wherein the solvent for the straight-chain polypeptide is one of a mixed solution of trifluoroacetic acid (TFA) and guanidine hydrochloride, an aqueous urea solution, acetonitrile, and phosphate buffered saline (PBS); and the solvent for the dimethylolurea is one of water, the acetonitrile, methanol, and N,N-dimethylformamide (DMF).

5. The method according to claim 4, wherein a concentration of the aqueous urea solution is 4 mol/L to 8 mol/L.

6. The method according to claim 5, wherein a concentration of the straight-chain polypeptide in the solvent for the straight-chain polypeptide is 1 mmol/L to 8 mmol/L, and a concentration of the dimethylolurea in the solvent for the dimethylolurea is 18 mmol/L to 80 mmol/L.

7. The method according to claim 6, the method comprising adding an acid reaction regulator to the dehydration-condensation reaction in the step (2); the acid reaction regulator is a TFA; and a volume ratio of a solution of the straight-chain polypeptide to the acid reaction regulator is 1:1 to 1:3.

8. The method according to claim 7, the method comprising conducting the dehydration-condensation reaction in the step (2) at 0° C. to 40° C. for 0 min to 10 min.

9. An anti-*Mycobacterium tuberculosis* drug in aqueous form comprising the polypeptide according to claim 1.

* * * * *